United States Patent [19]

Haddad et al.

[11] 4,261,364

[45] Apr. 14, 1981

[54] ELECTRIC WARM COMPRESS FOR OPHTHALMIC TREATMENT

[76] Inventors: Heskel M. Haddad, 1200 Fifth Ave., New York, N.Y. 10029; Roland Longarzo, P.O. Box 32, Valley Stream, N.Y. 11582

[21] Appl. No.: 6,813

[22] Filed: Jan. 26, 1979

Related U.S. Application Data

[63] Continuation of Ser. No. 840,338, Oct. 7, 1977, abandoned.

[51] Int. Cl.$^3$ .................. A61F 7/00

[52] U.S. Cl. .................. 128/399

[58] Field of Search .................. 128/254, 380, 399, 402, 128/791, 793

[56] References Cited

U.S. PATENT DOCUMENTS

| | | | |
|---|---|---|---|
| 1,015,991 | 1/1912 | Clark | 128/399 |
| 1,446,991 | 2/1923 | Richmond | 128/402 |
| 1,714,693 | 5/1929 | Renwick | 128/399 |
| 1,723,373 | 8/1929 | Roberts | 128/254 |
| 2,198,989 | 4/1940 | Cooley | 128/399 |
| 3,376,870 | 4/1968 | Yammamoto et al. | 128/793 |
| 3,644,705 | 2/1972 | Johnson | 128/402 |
| 3,768,485 | 10/1973 | Linick | 128/402 |
| 3,796,855 | 3/1974 | Brown et al. | 128/399 |

*Primary Examiner*—William E. Kamm
*Attorney, Agent, or Firm*—Blum, Kaplan, Friedman, Silberman & Beran

[57] ABSTRACT

A portable surgical compress heating device is provided. The device includes a thermo-electric element encapsulated within a housing which is placed over the compress to be heated. Conductors lead from the housing to a portable power supply to activate the thermo-electric element. The thermo-electric element is so arranged within the housing so as to provide a uniform transfer of heat to the compress.

9 Claims, 4 Drawing Figures

ELECTRIC WARM COMPRESS FOR OPHTHALMIC TREATMENT

This is a continuation of application Ser. No. 840,338, filed Oct. 7, 1977, now abandoned.

BACKGROUND OF THE INVENTION

This invention relates generally to a portable heating device for a surgical compress and especially to a heating device utilized in opthalmic surgery. A variety of surgical procedures which involve the use of a compress require for therapy that the compress be warm. This requirement for warmth or heating of the compress has required various means to provide a constant heat flow to the compress. This requirement for a flow of heat has sometimes limited the patient's mobility. The instant invention provides a compact, portable heating device for a surgical compress which provides an even and constant flow of heat.

SUMMARY OF THE INVENTION

Generally speaking, in accordance with the invention, a portable surgical compress heating device is provided. The device has a thermo-electric element encapsulated in a housing which is placed over the compress to be heated. A portable battery pack supplies the power for the thermo-electric device and is connected to the housing by conductive wires. The arrangement of the thermo-electric element within the housing provides for a constant flow of heat over the entire surface of the housing.

Accordingly, it is an object of this invention to provide an improved heating device for a surgical compress that is portable.

Another object of this invention is to provide an improved heating device for a surgical compress which is compact.

A further object of this invention is to provide an improved heating device for a surgical compress which permits a constant flow of evenly distributed heat to the compress.

Another object of this invention is to provide an improved heating device for a surgical compress that is simple and economical to manufacture and use.

Still other objects and advantages of the invention will in part be obvious and will in part be apparent from the specification.

The invention accordingly comprises the features of construction, combination of elements and arrangement of parts which will be exemplified in the construction hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which.

DESCRIPTION OF THE PREFERRED EMBODIMENTS

Figure 1:
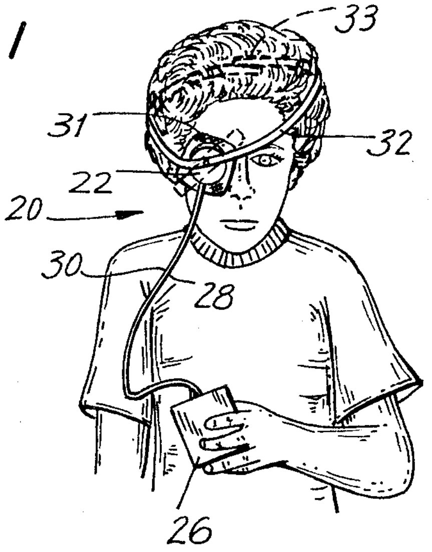
FIG. 1 is an elevational view of the device in use with an eye compress.
Figure 4:
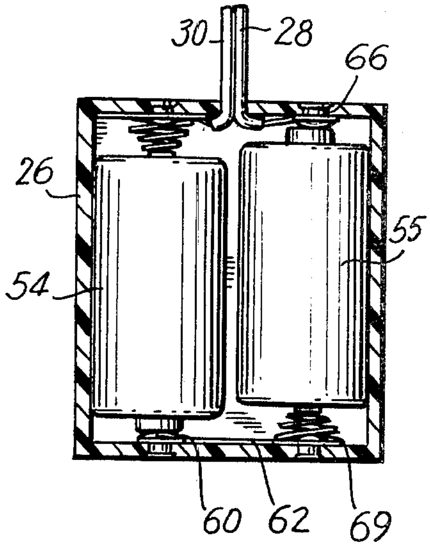
FIG. 4 is a sectional view of the battery pack.
Figure 2:
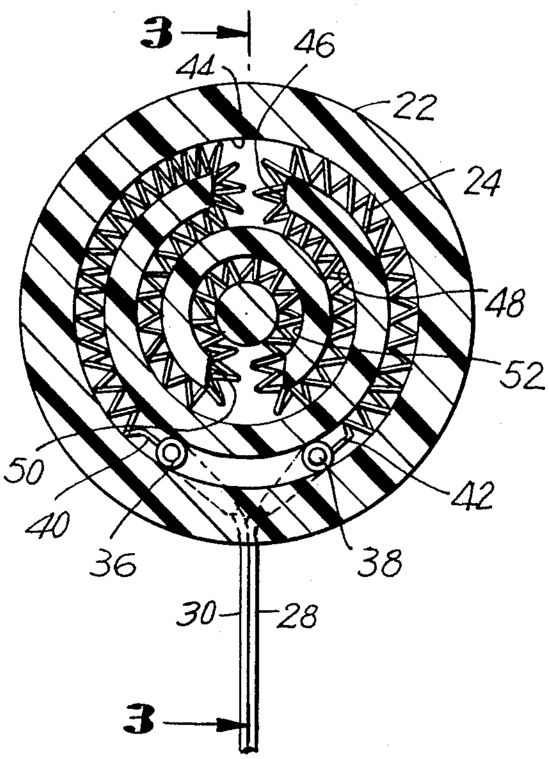
FIG. 2 is a sectional view of the housing containing the thermo-electric element.

The drawings illustrate a portable surgical compress heating device generally indicated at 20 that includes a housing 22 in which a thermo-electric element such as a heating coil 24 is encapsulated. In this embodiment, housing 22 is configured to fit within an human eye socket. A portable battery pack 26 is electrically coupled to heating coil 24 by means of wires 28 and 30. In use, housing 22 containing heating coil 24 is placed over the surgical compress 30 such as that shown in FIG. 1. Heating device 20 may be attached to compress 31 by means of an elastic strap 32 including hook and loop section 33 to join same together around the patients head or may be attached to the compress by other means such as by taping housing 22 to compress 31.

Figure 3:
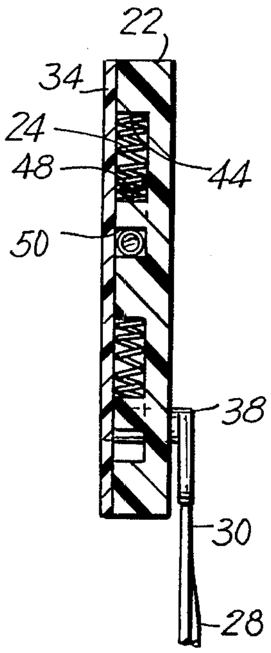
FIG. 3 is a sectional view taken along line 3—3 of FIG. 2.

Heating coil 24 is arranged within housing 22 so as to provide an even transfer of heat from it to the cover-plate 34 of housing 22. Cover plate 34 may be joined to housing 22 by any suitable means such as glue, fasteners etc. or may be integrally molded therewith. Wires 28, 30 leading from battery pack 26 are joined to terminals 36, 38 respectively by any known means such as blades and sockets or soldering. Terminals 36, 38 are joined to ends 40, 42, respectively of heating coil 24. Heating coil 24 is arranged within three concentric interconnected circular channels within housing 24. Terminals 36, 38 are arranged within outer concentric circular channel 44 which has an opening 46 so that heating coil 24 may enter a second concentric circular channel 48 which in turn has an opening 50 leading to innermost concentric channel 52 which surrounds the center of housing 24. As shown in FIG. 3, channels 44, 48 and 52 are each disposed closer to the cover-plate 34 of housing 24 to maximize heat transfer to compress 30. The use of concentric interconnected channels in which heating coil 24 is disposed permits an even distribution of heat over cover-plate 34 of housing 22 to permit a like even heat transfer to compress 30.

Wires 28, 30 lead from terminals 36, 38 respectively to battery pack 26 which is illustrated containing common dry cells 54. Wire 30 is joined to coil 56 which contacts the negative terminal of battery 54. The positive terminal of battery 54 contacts post 60 which is electrically connected by means of wire 62 with coil 64 contacting negative terminal of battery 55. The positive terminal of battery 55 contacts post 66 which is joined to wire 28 to form a series connection of batteries 54, 55 with heating coil 24. While normal dry cells have been illustrated, it is understood that any form of portable power supply such as other types of batteries or other forms of current supply could be substituted for battery pack 26.

The embodiment of the heating device illustrated is especially suitable for use in chalazion therapy used in ophthalmic surgery. For this use, a heating coil 24 generating a heat of 110°-120° F. is appropriate. Thus, heating coil 24 would be constructed from a suitable type of electrical resistance wire which would operate in this temperature range with battery pack 26. The amount and gauge of wire used in heating coil 24 is such that the current drain is not high. Since the operating temperature is not high, any plastic suitable for use at this temperature is usable for forming molded housing 22 and cover-plate 34. However, the instant invention is not limited in its application to ophthalmic surgery but rather is adaptable wherever a warm compress is needed such as the treatment of small boils. For use in other such treatments a variety of different sized and configured housings and heating coils operating at different temperatures may be used and such other configurations are within the scope of the invention.

It will thus be seen that the objects set forth above, among those made apparent from the preceding description, are efficiently attained and, since certain changes may be made in the above construction without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A heating device for a compress for use in ophthalmic treatment comprising a rigid housing dimensioned and shaped for receipt within the socket of a human eye and having a solid wall positioned to face the eye when the housing is positioned in an eye socket, a thermo-electric element disposed within said housing to permit the transfer of heat through said housing wall, said housing defining a waterproof container for said thermo-electric element, a portable battery pack, means for electrically connecting said battery pack to said thermo-electric element, said battery pack and said thermo-electric element being coordinately selected to produce heat of a low temperature suitable for opthalmic treatment, and strap means secured to said housing for extending about a user's head for releasably retaining said housing in the socket of an eye, whereby heat is transferred from said housing wall to the eye.

2. The heating device as claimed in claim 1, wherein said thermo-electric element comprises a heating coil.

3. A heating device as claimed in claim 2, wherein said housing includes a series of concentric interconnected circular channels, said heating coil being disposed within said channels.

4. A heating device as claimed in claim 3, wherein said housing is circular in overall configuration.

5. A heating device as claimed in claim 3, wherein said heating coil is disposed at a distance closer to one of the outer surfaces of said housing than the other opposite surface of said housing, said one outer surface of said housing being the outer surface of said wall positioned to face the eye.

6. A heating device as claimed in claim 5, wherein said housing is formed of a rigid plastic material, said wall being essentially planar.

7. A heating device as claimed in claim 1, wherein said means for electrically connecting said battery pack to said thermo-electric element comprises flexible wires.

8. A heating device as claimed in claim 1, wherein said strap means includes hook and loop means for joining said strap together.

9. A heating device as recited in claim 1, wherein said battery pack and thermo-electric element are selected to produce heat of a range from 110° F. to 120° F.

* * * * *